United States Patent
Cao et al.

(10) Patent No.: US 9,439,641 B2
(45) Date of Patent: Sep. 13, 2016

(54) EXPOSURE APPARATUS FOR POSTERIOR SPINAL MINIMALLY INVASIVE SCREW PLACEMENT SURGERY

(71) Applicant: THE FIRST AFFILIATED HOSPITAL OF NANJING MEDICAL UNIVERSITY, Nanjing, Jiangsu (CN)

(72) Inventors: Xiaojian Cao, Jiangsu (CN); Haijun Li, Jiangsu (CN); Jian Tang, Jiangsu (CN); Hao Xie, Jiangsu (CN)

(73) Assignee: THE FIRST AFFILIATED HOSPITAL OF NANJING MEDICAL UNIVERSITY (CN)

( * ) Notice: Subject to any disclaimer, the term of this patent is extended or adjusted under 35 U.S.C. 154(b) by 0 days.

(21) Appl. No.: 14/764,797

(22) PCT Filed: Nov. 13, 2013

(86) PCT No.: PCT/CN2013/087037
§ 371 (c)(1),
(2) Date: Jul. 30, 2015

(87) PCT Pub. No.: WO2014/117562
PCT Pub. Date: Aug. 7, 2014

(65) Prior Publication Data
US 2015/0366549 A1    Dec. 24, 2015

(30) Foreign Application Priority Data
Jan. 30, 2013   (CN) .......................... 2013 1 0035400

(51) Int. Cl.
*A61B 1/32*       (2006.01)
*A61B 17/02*      (2006.01)

(52) U.S. Cl.
CPC ........... *A61B 17/0218* (2013.01); *A61B 17/02* (2013.01); *A61B 17/025* (2013.01); *A61B 2017/0256* (2013.01)

(58) Field of Classification Search
CPC ................. A61B 17/025; A61B 2017/0256
USPC .................................. 600/184–246
See application file for complete search history.

(56) References Cited

U.S. PATENT DOCUMENTS 4,817,587 A * 4/1989 Janese ................ A61B 17/0293
600/210

(Continued)

FOREIGN PATENT DOCUMENTS

| CN | 2383475 Y | 6/2000 |
| CN | 2910132 Y | 6/2007 |

(Continued)

OTHER PUBLICATIONS

International Search Report; PCT/CN2013/087037; International Filing Date: Nov. 13, 2013; 3 Pgs.

*Primary Examiner* — Ellen C Hammond
*Assistant Examiner* — Christina Negrellirodrigue
(74) *Attorney, Agent, or Firm* — Schmeiser, Olsen & Watts, LLP

(57) ABSTRACT

An exposure apparatus for posterior spinal minimally invasive screw placement surgery includes a transverse process refractor and a facet joint retractor, is provided. The apparatus separates a gap between a multifidus muscle and a longissimus muscle, easily and atraumatically reach a screw placement position on a pedicle, accurately place the retractors, and thereafter locally form a screw placement tunnel space that externally extends 10 to 15 degrees. During a screw placement operation, the distal end of the transverse process refractor can straddle above the transverse process and is antagonistically tractive with the facet joint retractor so as to leave a sufficient space for the screw placement operation and to prompt a needle inlet point and direction for placing a pedicle screw. The distal end of the refractor employs a design of a recessed crescent type, protects local soft tissues during traction, and prevents the tissues from damage.

3 Claims, 2 Drawing Sheets

(56) References Cited

U.S. PATENT DOCUMENTS

| | | | | |
|---|---|---|---|---|
| 6,951,538 B2 * | 10/2005 | Ritland | ............ | A61B 17/1757 600/210 |
| 7,455,639 B2 * | 11/2008 | Ritland | ................ | A61B 17/02 600/201 |
| 2002/0123668 A1 | 9/2002 | Ritland | | |
| 2011/0201897 A1 | 8/2011 | Bertagnoli et al. | | |

FOREIGN PATENT DOCUMENTS

| | | |
|---|---|---|
| CN | 201290705 Y | 8/2009 |
| CN | 103110437 A | 5/2013 |

* cited by examiner

EXPOSURE APPARATUS FOR POSTERIOR SPINAL MINIMALLY INVASIVE SCREW PLACEMENT SURGERY

CROSS-REFERENCE TO RELATED APPLICATIONS

This application claims priority to PCT Application No. PCT/CN2013/087037, having a filing date of Nov. 13, 2013, based off of Chinese Application No. 201310035400.1, having a filing date of Jan. 30, 2013 the entire contents of which are hereby incorporated by reference.

FIELD OF TECHNOLOGY

The following invention relates to an exposure apparatus for posterior spinal minimally invasive screw placement surgery, which belongs to the field of medical appliances.

BACKGROUND

Pedicle screw technology has been developed quickly since its introduction in 1980s and has been widely used in surgical treatment on affections such as spinal degeneration, spondylolisthesis, spinal stenosis, vertebral fracture, malformation, metastatic tumor of bone, spinal instability and the like. At present, the pedicle screw is one of the internal fixation instruments most widely used in a spine surgery, and methods for embedding the pedicle screw mainly include: 1. a posterior medisection screw placement surgery, which is a conventional surgery manner, is extensive in clinical application presently, and widely accepted by most of the clinicists, but it has some major defects of larger surgery wound, difficult exposure of a needle inlet point at the pedicle, more bleeding, longer postoperative recovery time for the patients, multiple combination of atrophy of longissimus muscle and multifidus muscle, instability due to ligament damage, and long-dated lumbago left on partial sufferers; 2. minimally invasive spine technology, i.e., posterior channel aided minimally invasive screw placement technology, which conducts the operation of placing a spinal pedicle screw with the help of such special surgery appliances and instruments like medical images, aided channel expansion and microscopic endoscope or the like, achieves the optimal therapeutic effect with minimal injury, and has the advantages of short surgical incision, small wound, less bleeding, rapid postoperative function recovery, and reduction of incidence of postoperative pains on the waist and back as compared with the conventional method. But presently, it has not been widely applied and popularized for being applied in clinic for almost 30 years since it is invented due to the expensive supporting instruments and relatively flat learning curves, and particularly, it is only limited to be developed at the spine surgery of tertiary hospitals at home presently.

A new minimally invasive technology which has the advantages of short surgical incision, small wound, less bleeding, rapid postoperative function recovery that are similar to a minimally invasive surgery, is simple and effective, and is easy to grasp, is needed in clinic presently. The inventor redesigns a set of surgical manner and surgical instrument, and improves the posterior spinal minimally invasive technology, which is simple and convenient, easier to grasp, has smaller wound than that of the conventional minimally invasive surgery, while the exposure apparatus for posterior spinal small incision pedicle screw placement is just a part thereof.

The conventional posterior spinal minimally invasive screw placement technology generally employs a kirschner wire to puncture and position the pedicle and then incise the skin, use an expander to expand from small to big in sequence till obtaining a satisfactory size, wherein the puncture approach may deviate a gap between the multifidus muscle and the longissimus muscle and enter the multifidus muscle or the longissimus muscle to cause injury of the multifidus muscle and the longissimus muscle, and meanwhile, the expansion process thereof is to tear and draw local muscles actually, which further aggravates the muscular injury.

SUMMARY

An aspect relates to an exposure apparatus which can assist to accurately, quickly and conveniently conduct pedicle screw placement during a posterior minimally invasive screw placement surgery, wherein the apparatus can be used to separate a gap between a multifidus muscle and a longissimus muscle under direct vision, and can easily and non-invasively reach a screw placement position on a pedicle. Meanwhile, during a screw placement operation, the distal end of the transverse process retractor can straddle above the transverse process and is antagonistically tractive with the facet joint retractor so as to leave a sufficient space for the screw placement operation and to prompt a needle inlet point and direction for placing the pedicle screw.

A further aspect relates to an exposure apparatus for posterior spinal minimally invasive screw placement surgery according to embodiments of the present invention including a transverse process retractor and a facet joint retractor used cooperatively with the transverse process retractor, the transverse process retractor consists of a first handle and a first retractor body, wherein the first retractor body is an L-shaped metal bar having an included angle of 100±10 degrees, which satisfies the demand of externally extending 10 to 15 degrees during screw placement, and facilitates the placement of the pedicle screw; one end of the first retractor is fixedly connected to the first handle, the other end of the first retractor bends towards the direction of the first handle, and the end is provided with a crescent type recess, so that the transverse process retractor can easily straddle above the transverse process during the surgery and is located in the center of the transverse process; the facet joint refractor consists of a second handle and a second refractor body, wherein the second retractor body is an L-shaped metal bar having an included angle of 80±10 degrees, which satisfies the demand of the characteristic of holding multifidus muscle between the inside of an approach and the spinous process as well as externally extending 10 to 15 degrees during screw placement, facilitates the exposure of a surgical approach during surgery, and protects the inside muscle and facilitates the placement of the pedicle screw; one end of the second retractor body is fixedly connected to the second handle, the other end of the second retractor body bends towards the direction of the second handle, and the end is provided with a crescent type recess, so that a screw placement position can be easily exposed, and injury of local facet joint caused by contact of the retractor will not be increased.

As a further improvement of the foregoing technical solution, both the first retractor body and the second refractor body include a horizontal segment and a vertical segment, wherein a folded angle of 16S±15 degrees is formed between the first handle and the second handle, and the horizontal segment thereof, both the first handle and the second handle are located at one side of the horizontal segment opposite to the vertical segment so as to be convenient for holding during traction in the surgery, and reduce the influences of tissues surrounding an incision placing the retractor; the other ends of the first retractor body and the second retractor body respectively bend by 10±10 degrees towards the directions of the first handle and the second handle respectively, and the bending lengths of the first retractor body and the second retractor body are 5±3 mm.

As a further improvement of the foregoing technical solution, both the connected ends of the first handle and the second handle are fishmouth shaped flat structures, which avoid the oppression of the retractor on the tissues during the surgery, and are beneficial for operating the surgery; both the thicknesses of the first retractor body and the second retractor body are 2±1 mm, and both the widths thereof are 12±5 mm; and both the lengths of the horizontal segment of the first refractor body and the second retractor body are 100±50 mm.

Further, the length of the vertical segment of the first retractor body is 60±10 or 75±5 mm; and the length of the vertical segment of the second retractor body is 50±10 or 65±5 mm.

Further, the outer surfaces of the holding portions of the first handle and the second handle are subject to roughened treatment, which are convenient for holding during the surgery.

Further, the outside of the vertical segment of the transverse process retractor is provided with a prompt line for prompting a needle inlet point and direction for placing a pedicle screw. After the transverse process retractor is accurately placed during the surgery, the pedicle screw can be placed according to the prompt direction on the retractor.

Compared with the prior art, embodiments of the present invention have the advantageous effects that:

(1) The handle of embodiments of the present invention is roughened, which is convenient for the surgeon to hold; the fishmouth shaped design of the connected ends of the handle avoids the oppression injury of the retractor on the tissues; and the folded angle of about 165 degrees employed between the handle and the retractor body enables the holding portion of the handle upwarped, thus reducing the influences of tissues surrounding the incision on the retractor.

(2) Embodiments of the invention are designed according to the characteristic of local surgical approach soft tissues and the characteristic of local bone structures, which is designed rationally, is simple and convenient to operate, has a proper width that is convenient to accurately separate the gap between the multifidus muscle and the longissimus muscle under direction vision at the approach of the posterior spinal small incision screw placement surgery, and prevents the muscles from damage.

(3) After the retractor is accurately placed when finishing the dissection of the surgical approach, the design of the 80-degree angle of the facet joint retractor and the design of the 100-degree angle of the transverse process retractor can locally form a tunnel space that externally extends 10 to 15 degrees, which meets with the requirements of externally extending 10 to 15 degrees during pedicle screw placement, and is convenient to place the pedicle screw using a small incision.

(4) The arc-shaped recessed crescent type design used according to the characteristic of the facet joint at the distal end of the facet joint retractor can easily expose the screw placement position, and does not increase the injury of the soft tissues and bone structures at the positions in touch with the retractor.

(5) The arc-shaped recessed crescent type design used at the contact position of the transverse process retractor and the transverse process prevents local tissues from damage during surgery, and meanwhile the transverse process retractor can easily straddle above the transverse process during surgery, is located at the center of the transverse process, and prompts the needle inlet position for the pedicle screw placement according to the special relationship between the transverse process position and the screw placement position (generally a lumbar vertebra is the intersection point of the outer rim of the facet joint and the center of the transverse process).

(6) Embodiments of the present invention are simple and convenient to operate, facilitates the pedicle screw placement operation, and meanwhile, can shorten the operation time apparently, reduce the injury of local soft tissues during the surgery, and in particular, can accurately prompt the screw placement approach while exposing the surgical approach and improve the screw placement accuracy.

BRIEF DESCRIPTION

DETAILED DESCRIPTION

The technical solution of embodiments of the present invention will be described in details hereinafter, but the protection scope of the present invention is not limited to the embodiment.

Figure 1:
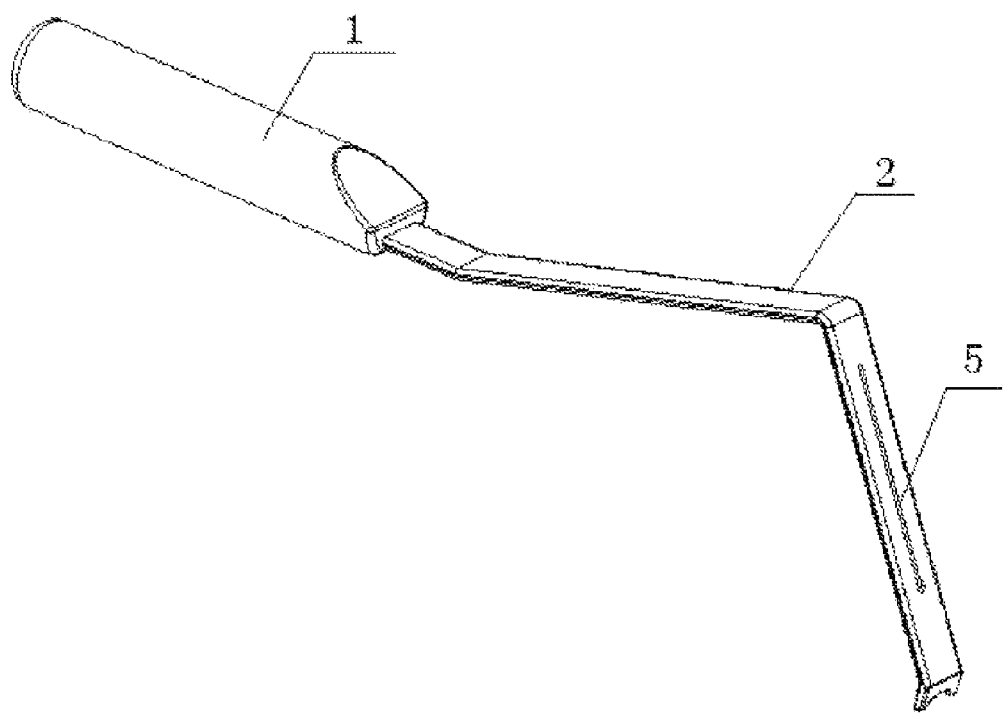
FIG. 1 is a schematic illustration of an embodiment of a transverse process retractor.
Figure 2:
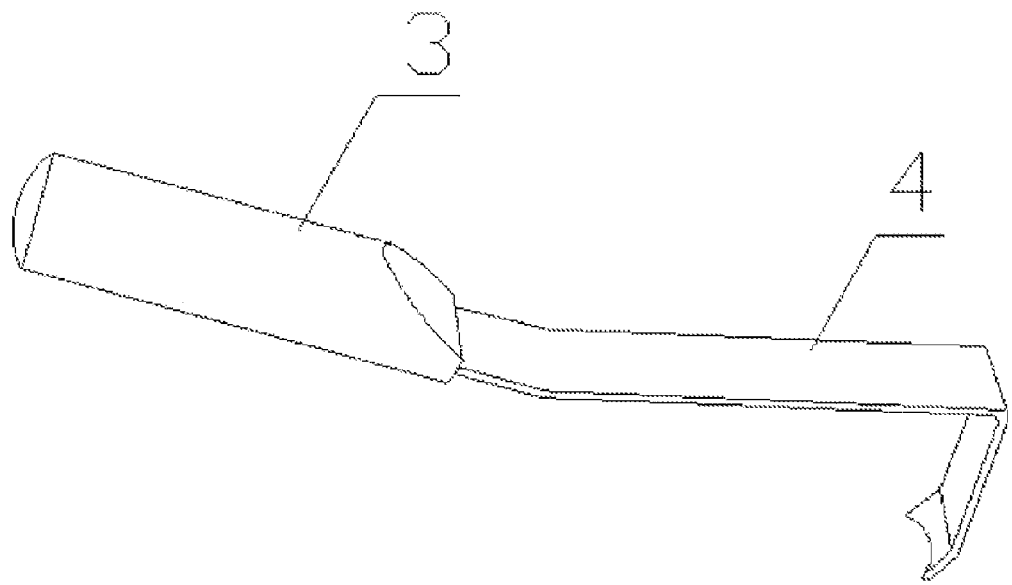
FIG. 2 is a schematic illustration of an embodiment of a facet joint retractor.
Figure 3:
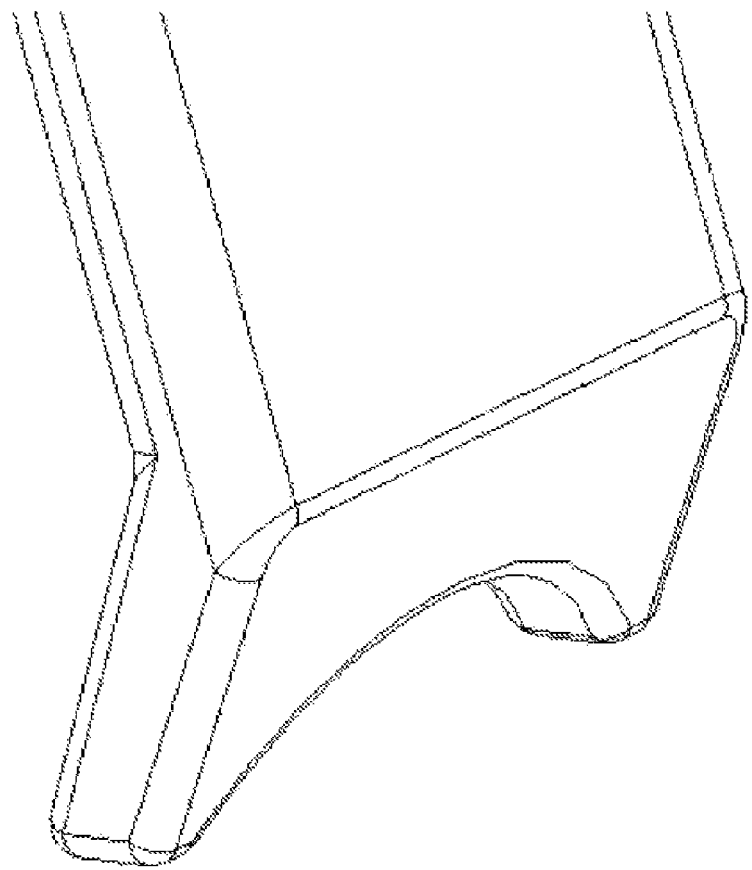
FIG. 3 is a schematic illustration of an embodiment of a crescent type recess of the transverse process retractor and the facet joint retractor.

Embodiment 1: as shown in FIG. 1 and FIG. 2, an exposure apparatus for posterior spinal minimally invasive screw placement surgery includes a transverse process retractor and a facet joint retractor used cooperatively with the transverse process retractor.

The transverse process retractor consists of a first handle 1 and a first retractor body 2, wherein the first retractor body 2 is an L-shaped metal bar having an included angle of 100 degrees, one end of the first retractor body 2 is fixedly connected to the first handle 1, the other end of the first retractor bends towards the direction of the first handle 1, and the end is provided with a crescent type recess.

The facet joint retractor consists of a second handle 3 and a second retractor body 4, wherein the second retractor body 4 is an L-shaped metal bar having an included angle of 80 degrees, one end of the second retractor body 4 is fixedly connected to the second handle 3, the other end of the second retractor body bends towards the direction of the second handle 3, and the end is provided with a crescent type recess.

Both the first retractor body 2 and the second retractor body 4 include a horizontal segment and a vertical segment, wherein a folded angle of 165 degrees is formed between the horizontal segment of the first handle I and the second handle 3, both the first handle 1 and the second handle 3 are located at one side of the horizontal segment opposite to the vertical segment, the other ends of the first retractor body 2 and the second retractor body 4 respectively bend by 10±10 degrees towards the directions of the first handle 1 and the second handle 3 respectively, and both the bending lengths of the first retractor body and the second retractor body are 5±3 mm.

Both the connected ends of the first handle 1 and the second handle 3 are fishmouth shaped flat structures, both the lengths of the first handle 1 and the second handle 3 are 120 mm, wherein the length of the holding portion is 100 mm, both the firs handle and the second handle are circular columns having a diameter of 20 mm, and the outer surfaces of the holding portions of the first handle 1 and the second handle 3 are subject to roughened treatment. Both the thicknesses of the first retractor body 2 and the second retractor body 4 are 2 mm, and the widths thereof are both 12 mm; and both the lengths of the horizontal segments of the first refractor body 2 and the second retractor body 4 are 100 mm. The length of the vertical segment of the first retractor body 2 is 60 or 75 mm; and the length of the vertical segment of the second retractor body 4 is 50 or 65 mm.

The outside of the vertical segment of the transverse process retractor is provided with a prompt line 5 for prompting a needle inlet point and direction for placing a pedicle screw.

As described above, although the present invention has been represented and described with reference to specifically preferred embodiment, it cannot be interpreted as a limitation to the present invention itself. Various modifications in forms and details may be made thereto without departing from the spirit and scope of the present invention as set forth in the appended claims.

The invention claimed is:

1. An exposure apparatus for posterior spinal minimally invasive screw placement surgery comprising:
   a transverse process retractor; and
   a facet joint retractor used cooperatively with the transverse process retractor;
   wherein the transverse process retractor consists of a first handle and a first retractor body, the first retractor body is an L-shaped metal bar having an included angle of 100±10 degrees, one end of the first retractor body is fixedly connected to the first handle, the other end of the first retractor bends towards a direction of the first handle, and the end is provided with a crescent type recess;
   wherein the facet joint retractor consists of a second handle and a second retractor body, the second retractor body is an L-shaped metal bar having an included angle of 80±10 degrees, one end of the second retractor body is fixedly connected to the second handle, the other end of the second retractor body bends towards a direction of the second handle, and the end is provided with a crescent type recess;
   wherein both the first retractor body and the second retractor body comprise a horizontal segment and a vertical segment, wherein a folded angle of 165±15 degrees is formed between the first handle and the second handle, and the horizontal segments thereof, both the first handle and the second handle are located at one side of the horizontal segment opposite to the vertical segment thereof, the other ends of the first retractor body and the second retractor body bend by 10±10 degrees towards the directions of the first handle and the second handle respectively, and both the bending lengths of the first retractor body and the second retractor body are 5±3 mm;
   wherein the outside of the vertical segment of the transverse process retractor is provided with a prompt line for prompting a needle inlet point and direction for placing a pedicle screw;
   wherein both the connected ends of the first handle and the second handle are fishmouth shaped flat structures, both the thicknesses of the first retractor body and the second retractor body are 2±1 mm, and the widths thereof are both 12±5 mm; and both the lengths of the horizontal segments of the first retractor body and the second retractor body are 100±50 mm.

2. The exposure apparatus for posterior spinal minimally invasive screw placement surgery according to claim 1, wherein the length of the vertical segment of the first retractor body is 60±10 or 75±5 mm; and the length of the vertical segment of the second retractor body is 50±10 or 65±5 mm.

3. The exposure apparatus for posterior spinal minimally invasive screw placement surgery according to claim 1, wherein the outer surfaces of the holding portions of the first handle and the second handle are subject to roughened treatment.

* * * * *